United States Patent
Duc et al.

(10) Patent No.: US 10,292,429 B2
(45) Date of Patent: May 21, 2019

(54) HEATER ASSEMBLY FOR AN AEROSOL-GENERATING SYSTEM

(71) Applicants: Fabien Duc, Carouge (CH); Alain Tabasso, Essertines-sur-Yverdon (CH)

(72) Inventors: Fabien Duc, Carouge (CH); Alain Tabasso, Essertines-sur-Yverdon (CH)

(73) Assignee: Altria Client Services LLC, Richmond, VA (US)

(*) Notice: Subject to any disclaimer, the term of this patent is extended or adjusted under 35 U.S.C. 154(b) by 13 days.

(21) Appl. No.: 15/623,849

(22) Filed: Jun. 15, 2017

(65) Prior Publication Data

US 2017/0360100 A1    Dec. 21, 2017

Related U.S. Application Data

(63) Continuation of application No. PCT/EP2017/062303, filed on May 22, 2017.

(30) Foreign Application Priority Data

Jun. 20, 2016 (EP) .................................. 16175298

(51) Int. Cl.
| | | |
|---|---|---|
| A24F 11/00 | (2006.01) | |
| A24F 47/00 | (2006.01) | |
| H05B 3/26 | (2006.01) | |
| H05B 3/28 | (2006.01) | |
| A61M 15/06 | (2006.01) | |

(Continued)

(52) U.S. Cl.
CPC .......... *A24F 47/008* (2013.01); *A61M 11/042* (2014.02); *A61M 15/06* (2013.01); *H05B 3/265* (2013.01); *H05B 3/283* (2013.01); *H05B 3/84* (2013.01); *A61M 2205/3653* (2013.01); *A61M 2205/8206* (2013.01); *H05B 2203/013* (2013.01); *H05B 2203/021* (2013.01)

(58) Field of Classification Search
CPC ..... A24F 47/008; A24F 47/002; H05B 3/283; H05B 3/265
USPC .................................................. 131/328, 329
See application file for complete search history.

(56) References Cited

U.S. PATENT DOCUMENTS

| | | | | |
|---|---|---|---|---|
| 6,118,109 A | * | 9/2000 | Sako ................. | G03G 15/2064 219/216 |
| 2002/0078956 A1 | | 6/2002 | Sharpe et al. | |

(Continued)

FOREIGN PATENT DOCUMENTS

| | | |
|---|---|---|
| DE | 20308376 U1 | 2/2004 |
| WO | WO-2015/117702 A1 | 8/2015 |

OTHER PUBLICATIONS

Extended European Search Report application No. 16175298.5 dated Dec. 9, 2016.

(Continued)

*Primary Examiner* — Hae Moon Hyeon
(74) *Attorney, Agent, or Firm* — Harness, Dickey & Pierce, P.L.C.

(57) ABSTRACT

In an example embodiment, a heater assembly for an aerosol-generating system includes two glass substrates. Each of the glass substrates includes perforations. The heater assembly also includes a heater element, and the heater element is located between the two glass substrates. In another example embodiment, a method for manufacturing a heater assembly includes providing two perforated glass substrates.

18 Claims, 4 Drawing Sheets

(51) Int. Cl.
H05B 3/84 (2006.01)
A61M 11/04 (2006.01)

(56) References Cited

U.S. PATENT DOCUMENTS

| | | | |
|---|---|---|---|
| 2007/0240715 A1 | 10/2007 | Hill | |
| 2008/0023003 A1 | 1/2008 | Rosenthal | |
| 2014/0060554 A1* | 3/2014 | Collett | H05B 3/265 |
| | | | 131/328 |
| 2017/0303588 A1* | 10/2017 | Batista | A24F 47/008 |
| 2017/0318862 A1* | 11/2017 | Mironov | A24F 47/008 |
| 2017/0340010 A1* | 11/2017 | Bilat | H05B 6/00 |

OTHER PUBLICATIONS

International Search Report and Written Opinion dated Jul. 20, 2017, in corresponding International Application No. PCT/EP2017/062303.

International Preliminary Report on Patentability for corresponding International Application No. PCT/EP2017/062303 dated Dec. 25, 2018.

* cited by examiner

HEATER ASSEMBLY FOR AN AEROSOL-GENERATING SYSTEM

CROSS-REFERENCE TO RELATED APPLICATIONS

This application is a continuation of, and claims priority to, international application no. PCT/EP2017/062303, filed on May 22, 2017, and further claims priority under 35 U.S.C. § 119 to European Patent Application. No. 16175298.5, filed Jun. 20, 2016, the entire contents of each of which are incorporated herein by reference.

BACKGROUND

Field

Example embodiments relate to a heater assembly for an aerosol-generating system and an aerosol-generating system comprising the heater assembly.

Description of Related Art

Handheld electrically operated aerosol-generating systems may include a battery and electric circuitry, a cartridge comprising a supply of a liquid aerosol-forming substrate held in a liquid storage portion, and an electrically operated vaporiser. A mesh heater may be utilized as a vaporiser. Such a mesh heater is disclosed, for example, in WO 2015/117702 A1 the entire content of which is incorporated herein by reference thereto, in which the mesh heater is provided by a plurality of electrically conductive metal filaments.

SUMMARY

At least one example embodiment relates to a heater assembly for an aerosol-generating system.

In at least on example embodiment, a heater assembly for an aerosol-generating system comprises a perforated glass substrate including perforations; and a heater element. The heater element is located in at least one of in the glass substrate and on the glass substrate.

In at least one example embodiment, the perforations have a width ranging from about 1 micron to about 500 microns. In at least one example embodiment, the perforations have a width ranging from about 5 microns to about 250 microns. In at least one example embodiment, the perforations have a width ranging from about 10 microns to about 150 microns.

In at least one example embodiment, a distance between adjacent ones of the perforations of the glass substrate ranges from about 1 micron to about 1000 microns. In at least one example embodiment, the distance between adjacent ones of the perforations of the glass substrate ranges from about 5 microns to about 750 microns. In at least one example embodiment, the distance between adjacent ones of the perforations of the glass substrate ranges from about 10 microns to about 500 microns.

In at least one example embodiment, at least one of the heater element and the perforations of the glass substrate include at least one of a mesh and an array. An area of at least one of the mesh and the array is less than about 25 square millimetres. In at least one example embodiment, the area is about 15 square millimetres. About 25 percent of the surface area to about 56 percent of the surface area of at least one of the mesh and the array is fluid-permeable.

In at least one example embodiment, a length of the heater assembly is about 3 millimetres and a width of the heater assembly is about 5 millimetres.

In at least one example embodiment, the heater element is a thin film on the glass substrate.

In at least one example embodiment, the heater element is incorporated into the glass substrate, such that the heater element is isolated from an adjacent aerosol-forming substrate.

In at least one example embodiment, the heater element is provided within at least one of the perforations.

In at least one example embodiment, the heater assembly also includes two perforated glass substrates. The heater element is between the two perforated glass substrates.

At least one example embodiment relates to an aerosol-generating system.

In at least one example embodiment, an aerosol-generating system comprises a main body, a battery in the main body, electric circuitry in the main body, a mouthpiece in the main body, a liquid storage portion attachable to the main body, and a heater assembly in the main body. The heater assembly includes a perforated glass substrate including perforations and a heater element. The heater element is located in at least one of in the glass substrate and on the glass substrate.

In at least one example embodiment, the heater element is adjacent to the liquid storage portion when the liquid storage portion is attached to the main body.

In at least one example embodiment, the heater element is in the mouthpiece.

At least one example embodiment relates to a method for manufacturing a heater assembly for an aerosol-generating system.

In at least one example embodiment, a method for manufacturing a heater assembly for an aerosol-generating system, comprises providing a perforated glass substrate, and placing a heater element in at least one of in the glass substrate and on the glass substrate.

BRIEF DESCRIPTION OF THE DRAWINGS

Features described in relation to one example embodiment may equally be applied to other example embodiments.

Example embodiments will now be described with reference to the accompanying drawings.

DETAILED DESCRIPTION

Figure 1A:
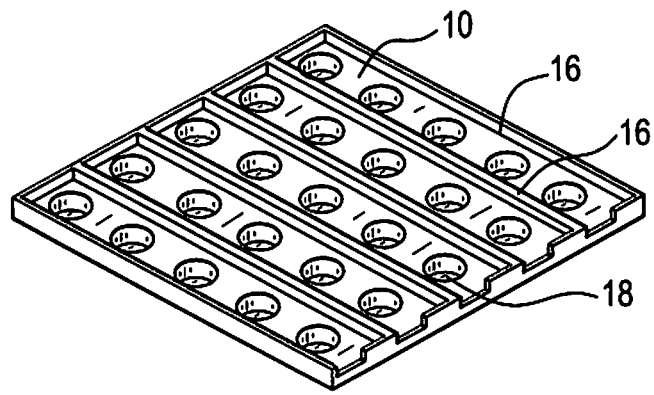
FIGS. 1a, 1b, and 1c are images of heater assemblies according to at least one example embodiment.

Example embodiments will become more readily understood by reference to the following detailed description of the accompanying drawings. Example embodiments may, however, be embodied in many different forms and should not be construed as being limited to the example embodiments set forth herein. Rather, these example embodiments are provided so that this disclosure will be thorough and complete. Like reference numerals refer to like elements throughout the specification.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when an element or layer is referred to as being "on", "connected to" or "coupled to" another element or layer, it can be directly on, connected or coupled to the other element or layer or intervening elements or layers may be present. In contrast, when an element is referred to as being "directly on", "directly connected to" or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings set forth herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-section illustrations that are schematic illustrations of idealized embodiments (and intermediate structures). As such, variations from the shapes of the illustrations as a result, for example, of manufacturing techniques and/or tolerances, are to be expected. Thus, these example embodiments should not be construed as limited to the particular shapes of regions illustrated herein, but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of this disclosure.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

Further, one or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

At least one example embodiment relates to a heater assembly for an aerosol-generating system.

In at least one example embodiment, a heater assembly for an aerosol-generating system includes a perforated glass substrate and a heater element. The heater element is in or on the glass substrate.

Glass has a high heat resistance. Thus, heating products may be reduced and/or substantially prevented when the heater element adjacent to the glass substrate is heated and vaporizes liquid aerosol-forming substrate. The heater element in or on the glass substrate may be heated to relatively high temperatures without damaging the glass substrate and without creating heating products due to burning of substrate or burning residues on the glass substrate.

Glass is also temperature stable, such that a multitude of heating and subsequent cooling processes may be performed by the heater element without the glass substrate degrading. Thus, the aerosol, which is generated by the heater assembly during vaporization of liquid aerosol-forming substrate, may be maintained at a consistent quality.

The perforated glass substrate and the heater element may be easily cleaned due to the surface characteristics of glass. Glass may have a smooth and hard surface so that the glass substrate is not damaged or harmed during cleaning of the glass substrate. Burning residues and contaminants may be cleaned from the surface of the glass substrate.

The perforated glass substrate may enable the liquid aerosol-forming substrate to flow through the glass substrate and to be vaporised by the heater element of the heater assembly. The glass substrate includes perforations which have a diameter that allows the liquid aerosol-forming substrate to flow through the glass substrate.

The glass substrate is a generally flat element having any suitable size and shape which allows its incorporation into a handheld system. An area of the glass substrate may be small. In at least one example embodiment, the area of the glass substrate is less than or equal to about 40 square millimeters, less than or equal to about 30 square millimetres, or less than or equal to about 20 square millimeters. A thickness of the glass substrate may be equal to or less than about 2 millimeters, equal to or less than about 1 millimeter, or equal to or less than about 0.5 millimeter.

The glass substrate may have a generally rectangular shape or a generally circular shape. In at least one example embodiment, the shape of the glass substrate is adapted to the dimensions of the liquid storage portion of the aerosol generating system.

In at least one example embodiment, the perforations of the glass substrate have a width ranging from about 1 micron to about 500 microns, from about 5 microns to about 250 microns, or from about 10 microns to about 150 microns.

Perforations in the glass substrate with such a width may allow a desired (or, alternatively predetermined) amount of liquid aerosol-forming substrate to flow through the glass substrate. The amount of liquid aerosol-forming substrate that may flow through the glass substrate is chosen such that enough aerosol is generated by the heater assembly.

A distance between the perforations of the glass substrate ranges from about 1 micron to about 1000 microns, from about 5 microns to about 750 microns, or from about 10 microns to about 500 microns.

The distance between the perforations may provide a dimensional stability of the glass substrate, such that the glass substrate is not prone to breaking during heating and cleaning and is not deformed easily. Distances between the perforations and perforations of the glass substrate with the above described width result in the surface area of the glass substrate being enlarged, while a relatively high dimensional stability of the glass substrate and the heater assembly may be provided.

In a least one example embodiment, about 15 percent to about 70 percent, about 20 percent to about 60 percent, or about 25 percent to about 55 percent of the glass substrate of the heater assembly may be fluid-permeable.

Amounts of liquid aerosol-forming substrate can permeate through the heater assembly to be vaporised, while the heater assembly is dimensionally stable. The heater element of the heater assembly may be in the form of a mesh or array, such that the surface area, which can be utilized for vaporising liquid aerosol-forming substrate, may be increased (e.g., optimized).

The heater element vaporises the liquid aerosol-forming substrate. The vaporised liquid aerosol-forming substrate forms an aerosol. The heater element is an electric resistance heater, which may be heated by an electric current. The heater element is made of an electrically conductive material such as aluminium or copper. Any other suitable electrically conductive material could be used as material for the heater element.

The heater element is on a surface of the glass substrate. In at least one example embodiment, the heater element is directly on the surface of the glass substrate. The heater element may be a coating or thin film, such as a metallic coating or metallic thin film.

In at least one example embodiment, the heater element may be in the glass substrate. The heater element may be incorporated into the glass substrate such that the heater element is encapsulated or encompassed by the glass substrate. The heater element may be provided as a metallic coating or thin metallic foil sandwiched between two layers of glass substrate. By encapsulating the heater element in the glass substrate or by sandwiching the heater element between two layers of glass substrate, the heater element is substantially protected from contact with the environment and in particular from contact with the liquid aerosol-forming substrate. As the liquid aerosol-forming substrate does not come into direct contact with the hot heater element, but only with the glass substrate, burning residues of liquid aerosol-forming substrate are less likely to be generated on the heater element during or after the vaporisation of the liquid aerosol-forming substrate.

By sandwiching the metallic heater thin film in between two layers of glass substrate delaminating of the metallic thin film can efficiently be reduced and substantially prevented.

The heater element may extend over the full width of the glass substrate. The heating element may also be provided as an array of linear heating strips or may form a mesh of heating strips. The heating elements could alternatively or additionally also be provided inside the perforations of the glass substrate.

In at least one example embodiment, the heater elements are within the perforations, only, and the heater elements may each have contact portions such that electric current may flow through the heater elements and heat the heater elements. If the heater elements are provided in the perforations only, the liquid is directly heated when passing the perforations. In at least one example embodiment, it is not necessary to heat the complete glass substrate to elevated temperatures. Instead only the limited amount of liquid that is drawn into the perforations is heated at a time. Accordingly, less energy is required in evaporation of the liquid aerosol-forming substrate.

The heater assembly may be provided with electrically conductive contact regions for contacting the heating elements provided in or on the glass substrate. The contact regions may be provided in the peripheral area of the glass substrate and may be adapted to establish electric contact to the control unit and the power supply of the aerosol-generating system.

At least one example embodiment relates to an aerosol-generating system.

In at least one example embodiment, an aerosol-generating system includes a main body and a heater assembly. In at least one example embodiment, the main body may comprise the heater assembly. The main body may further comprise a battery, electric circuitry, and a mouthpiece. In at least one example embodiment, the aerosol-generating system may be adapted to accommodate a replaceable or refillable liquid storage portion. The liquid storage portion may be attachable to the main body. The main body may comprise a sensor, such as a flow sensor. The flow sensor may be configured to detect a draw on the aerosol-generating system. Following this detection, the electric circuitry controls a flow of electric current from the battery through the heater element.

The heater assembly may be an integral part of the main body. The aerosol-generating system is configured, such that in the assembled state, the heater assembly is located adjacent to and in fluid communication with the liquid storage portion.

The liquid storage portion may comprise a housing having an opening, which may be sealed by a suitable sealing element. The sealing element may be a foil that can be removed before or upon insertion of the liquid storage portion into the aerosol-generating system. The liquid storage portion further comprises a liquid aerosol-forming substrate that may fully or partially be absorbed in a capillary element, provided within the liquid storage portion. The capillary element is within the liquid storage portion in direct vicinity to the opening of the housing of the liquid storage portion.

When inserted into the aerosol-generating system, the opening of the liquid storage portion is located adjacent to the heater assembly, such that the capillary element of the liquid storage portion is in direct contact with the heater assembly. In at least one example embodiment, the liquid aerosol-forming substrate may be conveyed from the liquid storage portion through the capillary element towards the heater assembly. Thus, the heater element is moisturized with liquid aerosol-forming substrate.

Suitable capillary materials may have a spongy or fibrous structure, which allows the liquid aerosol-forming substrate to be conveyed from the liquid storage portion to the heater assembly by capillary action. The capillary material may substantially prevent and/or reduced leakage of the liquid aerosol-forming substrate from the liquid storage portion.

The liquid storage portion may be part of a cartridge, wherein the cartridge comprises the liquid storage portion and a mouthpiece. The cartridge may be provided as a single-use cartridge which is disposed when the liquid aerosol-forming substrate in the liquid storage portion is depleted. In at least one example embodiment, the liquid storage portion may be a refillable liquid storage portion.

The mouthpiece portion may be connected to the main body of the device by a hinged connection. A hinged connection allows for a substantially simple insertion of the liquid storage portion into the device and removal of the cartridge from the device. The mouthpiece portion may be retained in a closed position by a clasp mechanism. The clasp mechanism may comprise a release button and may be configured to release the mouthpiece portion when the release button is depressed. The mouthpiece portion may retained in a closed position by other mechanisms such as a magnetic closure or a by using bi-stable hinge mechanism. Other means of connection of the mouthpiece portion to the main body are possible, such as screw-fitting or snap-fitting.

The mouthpiece portion may include an air inlet and an air outlet. The mouthpiece portion may include a baffle configured to direct air drawn through the mouthpiece portion from the inlet to the outlet past the vaporiser in the cartridge. By keeping all the airflow within the mouthpiece portion, the design of the main body may be simple, and only the mouthpiece portion of the device needs to be cleaned or replaced. Other airflow patterns are possible. Other orientations of the liquid storage portion within the device are possible.

The heater element may be in the mouthpiece of the main body. By placing the heater element in the mouthpiece of the main body, the heater element is directly adjacent to the liquid storage portion when the liquid storage portion is connected to the main body. The liquid aerosol-forming substrate from the liquid storage portion may be easily conveyed from the liquid storage portion to the heater element.

At least one example embodiment relates to a process for manufacturing a heater assembly for an aerosol-generating system.

In at least one example embodiment, a process comprises providing a perforated glass substrate and providing a heater element in or on the glass substrate.

The perforated glass substrate may be manufactured and provided by a phase separation process, a sintering process, or a sol-gel process.

When the heater element is provided on the glass substrate, the heater element may be an electrically conductive thin film. Thus the glass substrate is coated with the heater element such that the heater element is directly on the surface of the glass substrate. Consequently, the heater element may have essentially the same dimensions as the glass substrate. In other words, the heater element may comprise perforations with essentially the same dimensions as described above with reference to the glass substrate.

Furthermore, the heater element may be fluid permeable as described above with reference to the glass substrate.

When the heater element is provided in the glass substrate, a first portion of the glass substrate is provided. Then, the heater element is provided on the first portion of the glass substrate as a thin film. Subsequently, a second portion of the glass substrate is provided on the first portion and on the heater element. Thus, the first and second portions of the glass substrate together encapsulate or encompass the heater element. Only contact portions of the heater element are not encapsulated by the glass substrate. The heater element may be sandwiched between the first and second portion of the glass substrate. In the perforations of the glass substrate, the heater element may be exposed such that liquid aerosol-forming substrate may be vaporised in the perforations. The heater element may be sandwiched between the first and second portion of the glass substrate such that the heater element only comes into direct contact with the liquid aerosol-forming substrate within the perforations. Thus, the heater element may be directly exposed to the liquid aerosol-forming substrate within the perforations, while the rest of the heater element is isolated from the liquid aerosol-forming substrate by the first and second portion of the glass substrate.

Figure 1B:
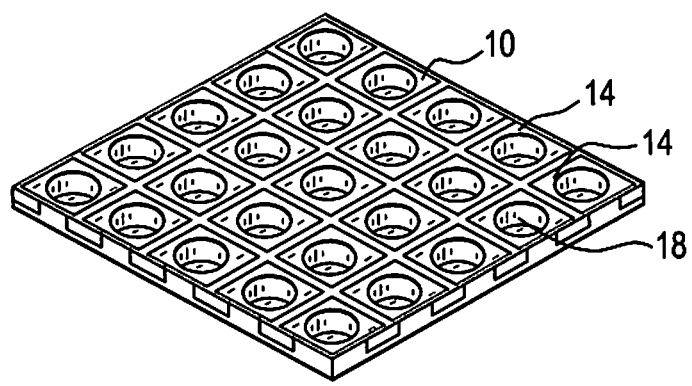

FIGS. 1a, 1b, and 1b are illustrations of a heater assembly according to at least one example embodiment. The heater assembly comprises a perforated glass substrate 10 and a heater element 12, 14, 16.

The glass substrate 10 is generally a flat rectangular element having a size of about 5×5 square millimetres and a thickness of about 1 millimeter. The small through holes or perforations 18 are provided in a regular pattern across the surface area of the glass substrate 10. The perforations 18 have a width of about 50 microns and are separated from each other by a distance of about 50 microns.

The heating element 12, 14, 16 is between the perforations 18. In FIG. 1a the heating element 12, 14, 16 is provided as parallel strips 16 of a conductive metallic thin film that are provided between alternating rows of perforations 18.

In FIG. 1b the heating element 12, 14, 16 is in the form of parallel strips and transversal strips 14 of a conductive metallic thin film that form a heating mesh or heating grid wherein each cell of the mesh comprises one perforation 18.

Figure 1C:
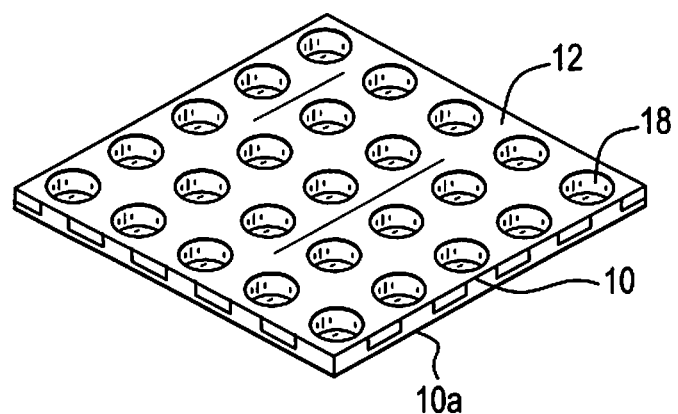

In FIG. 1c the heating element 12, 14, 16 is in the form of a uniform thin film 12 provided on the surface area of the glass substrate 10 surrounding the perforations 18.

Figure 2:
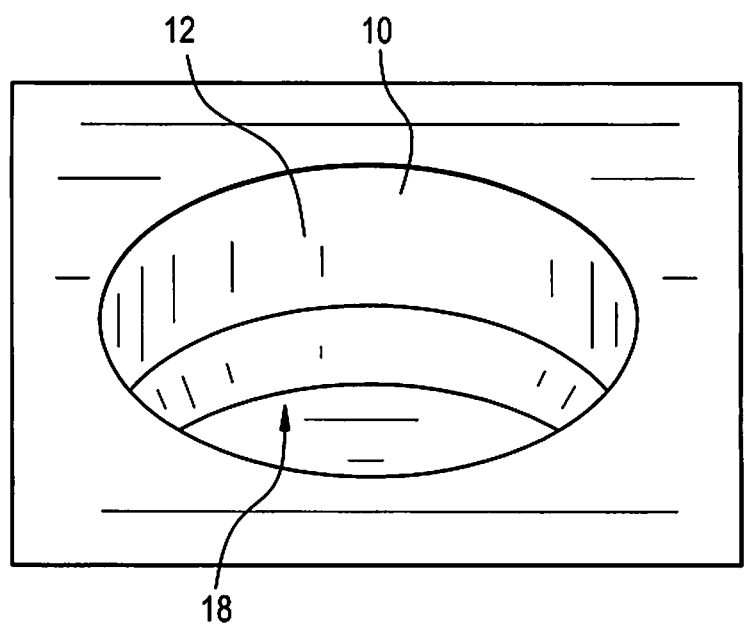
FIG. 2 is an illustration of a perforation of an embodiment of the heater assembly according to at least one example embodiment.

FIG. 2 is an enlarged view of a single perforation 18. As shown in FIG. 2, the metallic heating thin film 12 may also extend within the periphery of the perforations 18.

In FIGS. 1a, 1b, 1c, and 2 the heater element 12, 14, 16 is on a surface of the glass substrate 10. In at least one example embodiment, the heater element 12, 14, 16 may also be within the glass substrate 10. In at least one example embodiment, the heater element 12, 14, 16 is sandwiched between two or more layers of glass substrate 10, 10a.

In at least one example embodiment, the heater element 12, 14, 16 does not extend completely to the peripheries of the perforations 18. Thus, the heater assembly may be configured such that contact between the heater element 12, 14, 16 and the liquid aerosol-forming substrate may be avoided and/or at least substantially reduced.

Figure 3:
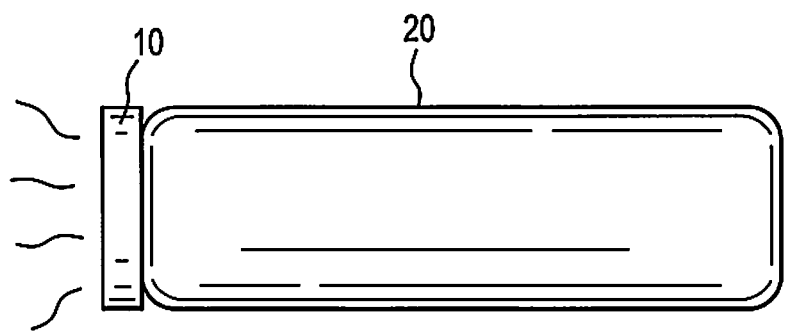
FIG. 3 is a sectional view of a heater assembly with a liquid storage portion according to at least one example embodiment.

The perforated heater assembly is brought into contact with a liquid storage portion 20 as depicted in FIG. 3. The liquid storage portion 20 may comprise a capillary material that contacts the heater assembly ensuring that the liquid aerosol-forming substrate is conveyed from the liquid storage portion 20 through the capillary element towards the heater assembly. Thus, the heater element 12, 14, 16 is at any time moisturized with liquid aerosol-forming substrate. Upon application of electric power to the heater element 12, 14, 16, the heater assembly is heated and the liquid aerosol-forming substrate is evaporated eventually forming an aerosol.

Figure 4A:
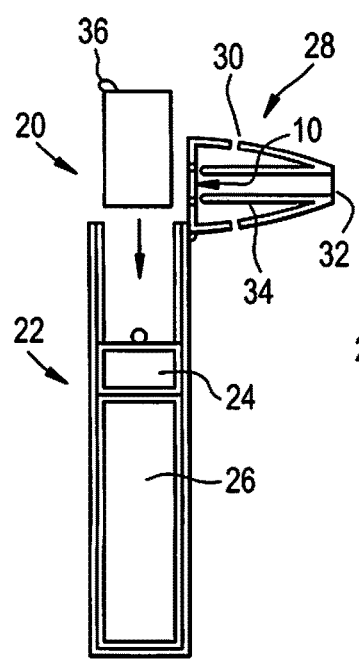
FIGS. 4a, 4b, and 4c are cross-sectional views of an aerosol-generating system according to at least one example embodiment.
Figure 4B:
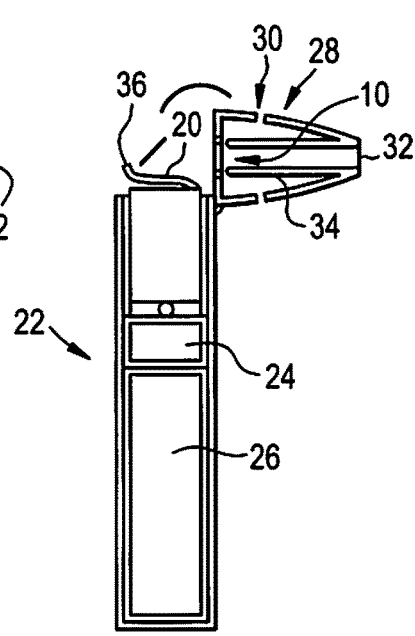
Figure 4C:
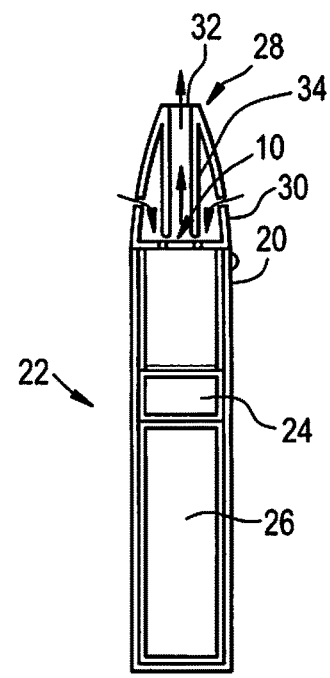

FIGS. 4a, 4b, and 4c are illustrations of an aerosol-generating system comprising a main body 22. The main body 22 comprises electric circuitry 24 and a battery 26. Furthermore, the main body 22 comprises the heater assembly as described herein. The battery 26 is electrically connected to the heater element 12, 14, 16 by contact portions of the heater element 12, 14, 16. The electric circuitry 24 controls the flow of electric current from the battery 26 to the heater element 12, 14, 16 such that the heater element 12, 14, 16 is heated when the aerosol-generating system is activated. In order to activate the aerosol-generating system, the aerosol-generating system can comprise a flow sensor, which detects a draw on the aerosol-generating system.

In FIGS. 4a, 4b, and 4c, the heater element 12, 14, 16 is in a mouthpiece 28. The mouthpiece 28 is part of the main body 22. The mouthpiece 28 is connected to the main body 22 by a hinged connection and can move between an open position and a closed position as shown. The mouthpiece portion 28 is placed in the open position to allow for insertion and removal of a liquid storage portion 20 and is placed in the closed position when the system is to be used to generate aerosol. The mouthpiece 28 comprises a plurality of air inlets 30 and an outlet 32. Air is drawn in through the air inlets 30. Internal baffles 34 are provided to force the air flowing through the mouthpiece 28 past the liquid storage portion 20. The internal baffles 34, which are integrally moulded with the external walls of the mouthpiece 28 ensure that, as air is drawn from the inlets 30 to the outlet 32, the air flows over the heater assembly where liquid aerosol-forming substrate is being vaporised. As the air passes the heater assembly, vaporised substrate is entrained in the airflow and cools to form an aerosol before exiting the outlet 32. In at least one example embodiment, the aerosol-forming substrate passes through the heater assembly by passing through the perforations 18 in the glass substrate 10 and the heater element 12, 14, 16 as it is vaporised.

The liquid storage portion 20 contains the liquid aerosol-forming substrate. The liquid storage portion 20 is replaceable. The liquid storage portion 20 is replaced once the liquid aerosol-forming substrate in the liquid storage portion 20 is depleted.

The aerosol-generating system can be activated by a sensor in the main body 22 which senses a negative pressure due to a draw on the mouthpiece 28. Then, the electric circuitry 24 controls a flow of electric current from the battery 26 to the heater element 12, 14, 16 of the heater assembly.

The liquid storage portion 20 comprises a sealing foil 36, which is removed before inserting the liquid storage portion 20 into the main body 22. The sealing foil 36 reduces and/or substantially prevents the liquid aerosol-forming substrate from leaking out of the liquid storage portion 20 before the liquid storage portion 20 is fully inserted into the main body 22 and the mouthpiece 28 is pivoted back in the closed position.

The exemplary embodiments described above illustrate but are not limiting. In view of the above discussed exemplary embodiments, other embodiments consistent with the above exemplary embodiments will now be apparent to one of ordinary skill in the art.

We claim:

1. A heater assembly for an aerosol-generating system comprising:
    two glass substrates, each of the two glass substrates including perforations; and
    a heater element, the heater element located between the two glass substrates.

2. The heater assembly according to claim 1, wherein the perforations have a width ranging from about 1 micron to about 500 microns.

3. The heater assembly according to claim 2, wherein the width ranges from about 5 microns to about 250 microns.

4. The heater assembly according to claim 3, wherein the width ranges from about 10 microns to about 150 microns.

5. The heater assembly according to claim 1, wherein a distance between adjacent ones of the perforations of at least one of the glass substrates ranges from about 1 micron to about 1000 microns.

6. The heater assembly according to claim 5, wherein the distance between adjacent ones of the perforations of at least one of the glass substrates ranges from about 5 microns to about 750 microns.

7. The heater assembly according to claim 6, wherein the distance between adjacent ones of the perforations of at least one of the glass substrates ranges from about 10 microns to about 500 microns.

8. The heater assembly according to claim 1, wherein the heater element includes a mesh, an array, or both a mesh and an array.

9. The heater assembly according to claim 8, wherein an area of the mesh, the array, or both the mesh and the array is less than about 25 square millimeters.

10. The heater assembly according to claim 9, wherein the area is about 15 square millimeters.

11. The heater assembly according to claim 8, wherein about 25 percent of the surface area to about 56 percent of the surface area of the mesh, the array, or both the mesh and the array is fluid-permeable.

12. The heater assembly according to claim 1, wherein a length of the heater assembly is about 3 millimeters and a width of the heater assembly is about 5 millimeters.

13. The heater assembly according to claim 1, wherein the heater element is a thin film.

14. The heater assembly according to claim 1, wherein the heater element is provided within at least one of the perforations.

15. An aerosol-generating system comprising:
    a main body;
        a battery in the main body,
        electric circuitry in the main body; and
        a mouthpiece in the main body;
    a liquid storage portion attachable to the main body; and
    a heater assembly in the main body, the heater assembly including,
        two glass substrates, each of the two glass substrates including perforations; and
        a heater element, the heater element located between the two glass substrates.

16. The aerosol-generating system according to claim 15, wherein the heater element is adjacent to the liquid storage portion when the liquid storage portion is attached to the main body.

17. The aerosol-generating system according to claim 15, wherein the heater element is in the mouthpiece.

18. A method for manufacturing a heater assembly for an aerosol-generating system, comprising:
    providing two perforated glass substrates; and
    placing a heater element between the two perforated glass substrates.

* * * * *